United States Patent
Cunningham et al.

(10) Patent No.: US 10,905,551 B2
(45) Date of Patent: Feb. 2, 2021

(54) RAPID EXCHANGE TRANSCATHETER VALVE DELIVERY SYSTEM

(71) Applicant: Medtronic Vascular, Inc., Santa Rosa, CA (US)

(72) Inventors: Kieran Cunningham, Ballybrit (IE); Marc Anderson, Ballybrit (IE); Declan Costello, Ballybrit (IE); Patrick Griffin, Ballybrit (IE)

(73) Assignee: Medtronic Vascular, Inc., Santa Rosa, CA (US)

(*) Notice: Subject to any disclaimer, the term of this patent is extended or adjusted under 35 U.S.C. 154(b) by 229 days.

(21) Appl. No.: 15/838,932

(22) Filed: Dec. 12, 2017

(65) Prior Publication Data
US 2018/0153695 A1 Jun. 7, 2018

Related U.S. Application Data

(63) Continuation of application No. 14/830,504, filed on Aug. 19, 2015, now Pat. No. 9,877,832.
(Continued)

(51) Int. Cl.
*A61F 2/24* (2006.01)
*A61M 25/01* (2006.01)
*A61F 2/95* (2013.01)

(52) U.S. Cl.
CPC ............ *A61F 2/2436* (2013.01); *A61F 2/243* (2013.01); *A61F 2/2418* (2013.01); *A61F 2/9522* (2020.05);
(Continued)

(58) Field of Classification Search
CPC ...... A61F 2002/9505; A61F 2002/9522; A61F 2/2418; A61F 2/243; A61F 2/2436;
(Continued)

(56) References Cited

U.S. PATENT DOCUMENTS 5,683,451 A 11/1997 Lenker
5,824,041 A 10/1998 Lenker et al.
(Continued)

FOREIGN PATENT DOCUMENTS

EP 2329799 6/2011
WO WO03002018 1/2003

OTHER PUBLICATIONS

PCT/US2015/046163, The International Search Report and the Written Opinion, dated Dec. 1, 2015.

*Primary Examiner* — Kathleen S Holwerda
*Assistant Examiner* — Brooke Labranche
(74) *Attorney, Agent, or Firm* — Dicke, Billig & Czaja, PLLC

(57) ABSTRACT

A delivery device for implanting a prosthetic heart valve. The device includes an inner shaft assembly, an outer sheath and a connector assembly. The inner shaft assembly defines a guide wire lumen. The outer sheath is slidably received over the inner shaft assembly, and forms an exit port proximate a distal end thereof. The connector assembly establishes a guide wire passageway between the guide wire lumen and the exit port. The connector assembly is configured to permit sliding movement of the outer sheath relative to the inner shaft assembly when deploying the prosthetic heart valve. The connector assembly can include first and second tubes that are slidable relative to one another in facilitating movement of the outer sheath relative to the inner shaft assembly.

13 Claims, 13 Drawing Sheets

Related U.S. Application Data

(60) Provisional application No. 62/040,486, filed on Aug. 22, 2014.

(52) U.S. Cl.
CPC ...... *A61F 2002/9505* (2013.01); *A61M 25/01* (2013.01); *A61M 2025/0175* (2013.01); *A61M 2025/0183* (2013.01)

(58) Field of Classification Search
CPC ......... A61F 2/2427; A61M 2025/0175; A61M 2025/0183; A61M 25/01
See application file for complete search history.

(56) References Cited

U.S. PATENT DOCUMENTS

| | | |
|---|---|---|
| 5,906,619 A | 5/1999 | Olson et al. |
| 5,957,949 A | 9/1999 | Leonhardt et al. |
| 2001/0031979 A1* | 10/2001 | Ricci .................. A61F 2/95 606/194 |
| 2003/0199963 A1 | 10/2003 | Tower et al. |
| 2005/0038495 A1 | 2/2005 | Greenan |
| 2006/0004439 A1 | 1/2006 | Spenser et al. |
| 2006/0074477 A1* | 4/2006 | Berthiaume ........ A61F 2/966 623/1.11 |
| 2007/0005131 A1 | 1/2007 | Taylor |
| 2007/0239266 A1 | 10/2007 | Birdsall |
| 2007/0250150 A1 | 10/2007 | Pal et al. |
| 2008/0082165 A1 | 4/2008 | Wilson et al. |
| 2009/0281619 A1 | 11/2009 | Le et al. |
| 2010/0179637 A1 | 7/2010 | Dorn et al. |
| 2011/0098805 A1 | 4/2011 | Dwork et al. |
| 2011/0264201 A1 | 10/2011 | Yeung et al. |
| 2012/0101561 A1 | 4/2012 | Porter |
| 2012/0239142 A1* | 9/2012 | Liu .................. A61F 2/2436 623/2.11 |
| 2012/0302952 A1 | 11/2012 | Kitada et al. |
| 2013/0231735 A1* | 9/2013 | Deem ................ A61F 2/243 623/2.11 |
| 2014/0180389 A1 | 6/2014 | Shin |

* cited by examiner

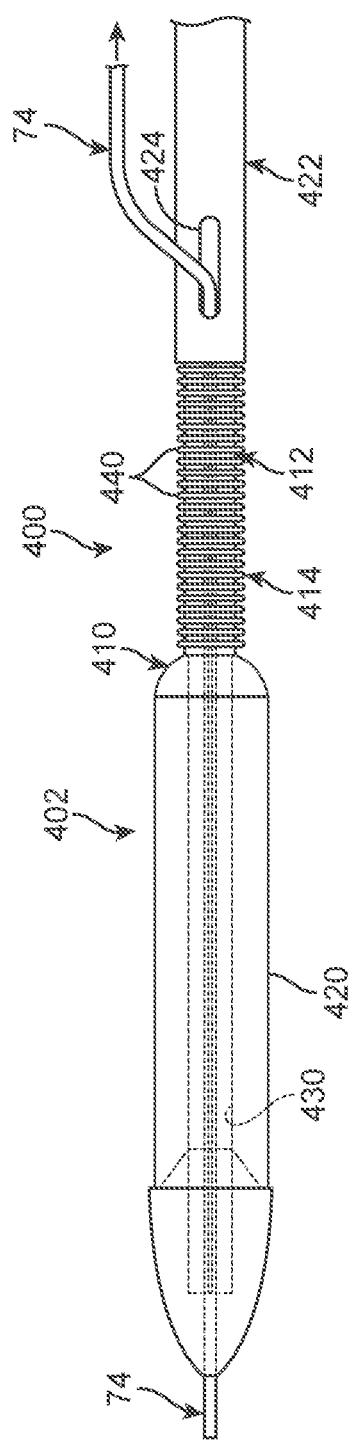
FIG. 9
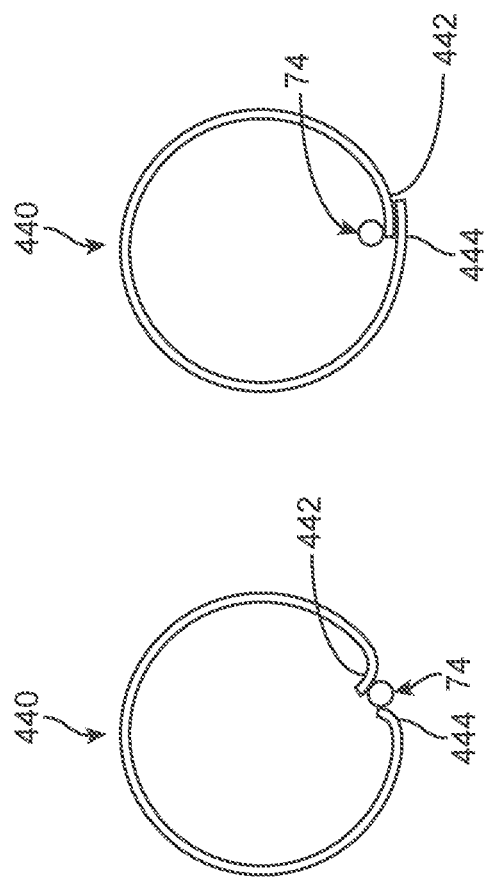
FIG. 10A
FIG. 10B
FIG. 10C

RAPID EXCHANGE TRANSCATHETER VALVE DELIVERY SYSTEM

CROSS REFERENCE TO RELATED APPLICATIONS

This application is a Continuation of and claims the benefit of U.S. patent application Ser. No. 14/830,504 filed Aug. 19, 2015, now allowed, which claims the benefit of the filing date of U.S. Provisional Patent Application Ser. No. 62/040,486, filed Aug. 22, 2014, the disclosures of which are herein incorporated by reference in their entirety.

BACKGROUND

The present disclosure relates to delivery systems for implanting transcatheter valves. More particularly, it relates to catheter-based, rapid exchange systems for implanting a stented prosthetic heart valve.

A human heart includes four heart valves that determine the pathway of blood flow through the heart: the mitral valve, the tricuspid valve, the aortic valve, and the pulmonary valve. The mitral and tricuspid valves are atrio-ventricular valves, which are between the atria and the ventricles, while the aortic and pulmonary valves are semilunar valves, which are in the arteries leaving the heart. Ideally, native leaflets of a heart valve move apart from each other when the valve is in an open position, and meet or "coapt" when the valve is in a closed position. Problems that may develop with valves include stenosis in which a valve does not open properly, and/or insufficiency or regurgitation in which a valve does not close properly. Stenosis and insufficiency may occur concomitantly in the same valve. The effects of valvular dysfunction vary, with regurgitation or backflow typically having relatively severe physiological consequences to the patient.

Diseased or otherwise deficient heart valves can be repaired or replaced using a variety of different types of heart valve surgeries. One conventional technique involves an open-heart surgical approach that is conducted under general anesthesia, during which the heart is stopped and blood flow is controlled by a heart-lung bypass machine.

More recently, minimally invasive approaches have been developed to facilitate catheter-based implantation of the valve prosthesis on the beating heart, intending to obviate the need for the use of classical sternotomy and cardiopulmonary bypass. In general terms, an expandable prosthetic valve is compressed about or within a catheter, inserted inside a body lumen of the patient, such as the femoral artery, and delivered to a desired location in the heart.

The heart valve prosthesis employed with catheter-based, or transcatheter, procedures generally includes an expandable multi-level frame or stent that supports a valve structure having a plurality of leaflets. The frame can be contracted during percutaneous transluminal delivery, and expanded upon deployment at or within the native valve. One type of valve stent can be initially provided in an expanded or uncrimped condition, then crimped or compressed about a balloon portion of an inner catheter or inner shaft. The balloon is subsequently inflated to expand and deploy the prosthetic heart valve. With other stented prosthetic heart valve designs, the stent frame is formed to be self-expanding. With these systems, the valved stent is crimped down to a desired size over an inner shaft and held in that compressed state within an outer sheath for transluminal delivery. Retracting the sheath from this valved stent allows the stent to self-expand to a larger diameter, fixating at the native valve site. In more general terms, then, once the prosthetic valve is positioned at the treatment site, for instance within an incompetent native valve, the stent frame structure may be expanded to hold the prosthetic valve firmly in place. One example of a stented prosthetic valve is disclosed in U.S. Pat. No. 5,957,949 to Leonhardt et al., which is incorporated by reference herein in its entirety.

In many transcatheter prosthetic heart valve delivery approaches, a guide wire is utilized to guide the catheter during delivery. The guide wire is preferably made of metal, and is routed through the tortuous path of the patient's vasculature to a desired location at the native valve site. Once the guide wire is in place, the delivery device is advanced over the guide wire and then operated to deploy the prosthetic valve. To accommodate the guide wire, the delivery device incorporates an "over-the-wire" design, forming a central guide wire lumen that extends an entire length of the outer sheath, for example from a distal-most opening in the inner shaft to a proximal opening or exit port at the device's handle. While well-accepted for stented prosthetic heart valve implant procedures, implementation of the over-the-wire approach may give rise to procedural complexities. For example, at least two clinicians are typically needed; one to operate the delivery device via the handle assembly and another to directly manage the guide wire outside of or beyond the handle assembly. Proper guide wire management can become increasingly intricate at various stages of the procedure, due in large part to the significant length of the guide wire outside of the patient. The delivery device is advanced over the pre-placed guide wire by inserting or "back-loading" a proximal end of the guide wire into the distal guide wire port, which in turns leads to the guide wire lumen, of the delivery device. The guide wire thus must be sized such that with the distal end of the guide wire located at the delivery site, a remaining length of guide wire outside of the patient is commensurate with (e.g., at least slightly longer than) a corresponding length of the delivery device, and in particular a length of the guide wire lumen. In other words, the guide wire employed with an over-the-wire system has a length at least double the length of the delivery device's outer sheath. This excessive length requires two clinicians, and increases the time necessary to load or unload the delivery device relative to the guide wire.

Other catheter-based procedures otherwise utilizing one or more guide wires, such as coronary catheter procedures, address some of the over-the-wire concerns by incorporating what is commonly referred to as a "rapid exchange" design. In a rapid exchange system, the guide wire occupies a lumen located only in the distal portion of the catheter. The guide wire exits the catheter through a proximal guide wire port that is located closer to the distal end of the catheter than to its proximal end, and extends in parallel along the outside of the proximal portion of the catheter. The rapid exchange configuration allows for the use of much shorter guide wires (as compared to over-the-wire designs), which enables a single clinician to handle the proximal end of the guide wire at the same time as the catheter at the point of entry into the patient.

Unfortunately, existing rapid exchange technology is not compatible with conventional stented prosthetic heart valve delivery devices. Unlike coronary catheters or other rapid exchange catheters having a single proximal guide wire port, the stented heart valve delivery device would effectively require at least two openings or ports on the proximal side: one in the inner shaft and a second in the outer sheath. In order to load the guide wire into the delivery device, a structured pathway connecting the two proximal side guide wire openings or ports would be necessary. Existing stented heart valve delivery devices do not contemplate rapid exchange, let alone provide requisite design features. Further, the operational requirements of stented heart valve delivery devices (e.g., retraction of the outer sheath relative to the inner shaft and the guide wire when deploying the valve) present distinct design obstacles for the structured pathway to be viable.

Although there have been multiple advances in transcatheter prosthetic heart valves and related delivery systems and techniques, a need exists for heart valve prosthesis delivery systems providing rapid exchange features.

SUMMARY

Some aspects of the present disclosure relate to a delivery device for implanting a stented prosthetic heart valve. The delivery device includes an inner shaft assembly, an outer sheath and a connector assembly. The inner shaft assembly defines a guide wire lumen. The outer sheath is slidably received over the inner shaft assembly, and forms a guide wire exit port near a distal end thereof. The connector assembly establishes a guide wire passageway between the guide wire lumen and the guide wire exit port. In this regard, the connector assembly is configured to permit sliding movement of the outer sheath relative to the inner shaft assembly when deploying the stented prosthetic heart valve. In some embodiments, the connector assembly includes first and second tubes that collectively establish the guide wire passageway and are slidable relative to one another in facilitating movement of the outer sheath relative to the inner shaft assembly.

BRIEF DESCRIPTION OF THE DRAWINGS

FIG. 9 is a simplified side view of portions of another stented prosthetic heart valve delivery system in accordance with principles of the present disclosure;

FIG. 10A is a side view of a clip component useful with the system of FIGS. 9; and FIGS. 10B and 10C are side views illustrating insertion of a guide wire into the clip of FIG. 10A.

DETAILED DESCRIPTION

Figure 1A:
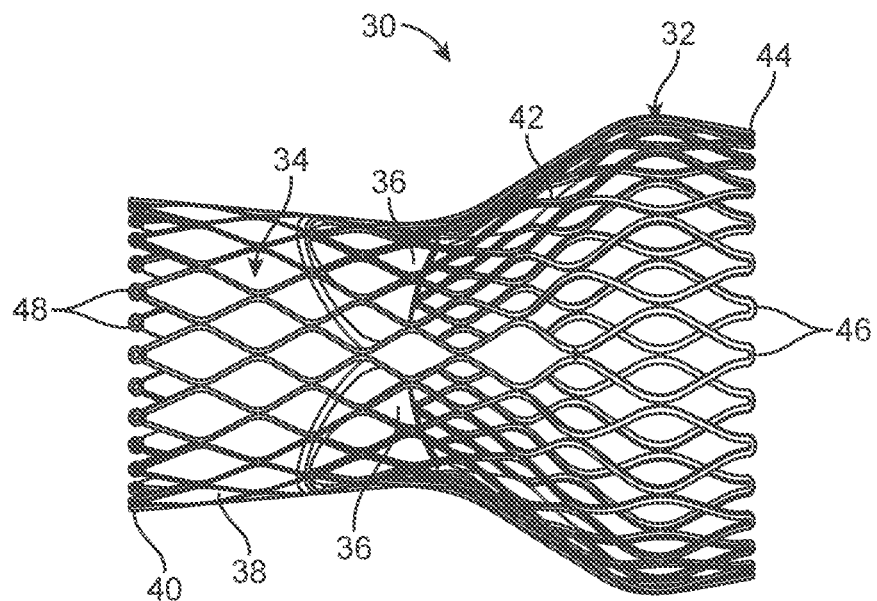
FIG. 1A is a side view of a stented prosthetic heart valve useful with systems, devices and methods of the present disclosure and in a normal, expanded condition.

Specific embodiments of the present disclosure are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician. As used herein with reference to an implanted valve prosthesis, the terms "distal", "outlet", and "outflow" are understood to mean downstream to the direction of blood flow, and the terms "proximal", "inlet", or "inflow" are understood to mean upstream to the direction of blood flow. In addition, as used herein, the terms "outward" or "outwardly" refer to a position radially away from a longitudinal axis of a frame of the valve prosthesis or delivery device and the terms "inward" or "inwardly" refer to a position radially toward a longitudinal axis of the frame of the valve prosthesis or delivery device. As well the terms "backward" or "backwardly" refer to the relative transition from a downstream position to an upstream position and the terms "forward" or "forwardly" refer to the relative transition from an upstream position to a downstream position.

As referred to herein, stented transcatheter prosthetic heart valves useful with and/or as part of the various systems, devices and methods of the present disclosure may assume a wide variety of different configurations, such as a bioprosthetic heart valve having tissue leaflets or a synthetic heart valve having polymeric, metallic or tissue-engineered leaflets, and can be specifically configured for replacing any of the four valves of the human heart. Thus, the stented prosthetic heart valve useful with the systems, devices, and methods of the present disclosure can be generally used for replacement of a native aortic, mitral, pulmonic or tricuspid valve, or to replace a failed bioprosthesis, such as in the area of an aortic valve or mitral valve, for example.

In general terms, the stented prosthetic heart valves of the present disclosure include a stent or stent frame maintaining a valve structure (tissue or synthetic), with the stent frame having a normal, expanded condition or arrangement and collapsible to a compressed condition or arrangement for loading within a delivery device. The stent frame is normally constructed to self-deploy or self-expand when release from the delivery device. In other embodiments, stent frames useful with systems and devices of the present disclosure have a balloon-expandable configuration as is known in the art. The stents or stent frames are support structures that comprise a number of struts or wire segments arranged relative to each other to provide a desired compressibility and strength to the prosthetic heart valve. The struts or wire segments are arranged such that they are capable of transitioning from a compressed or collapsed condition to a normal, radially expanded condition. The struts or wire segments can be formed from a shape memory material, such as a nickel titanium alloy (e.g., Nitinol™). The stent frame can be laser-cut from a single piece of material, or can be assembled from a number of discrete components.

Figure 1B:
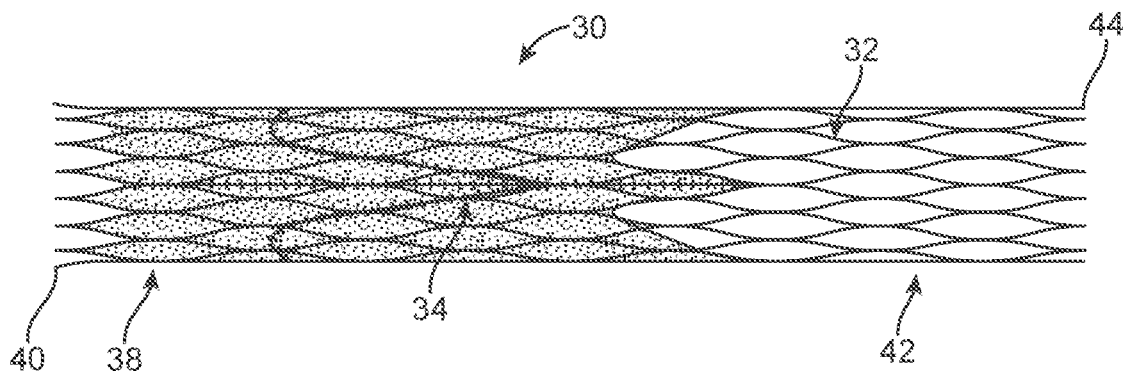
FIG. 1B is a side view of the prosthetic heart valve of FIG. 1A in a compressed condition.

With the above understanding in mind, one simplified, non-limiting example of a stented prosthetic heart valve 30 useful with systems, devices and methods of the present disclosure is illustrated in FIG. 1A. As a point of reference, the prosthetic heart valve 30 is shown in a normal or expanded condition in the view of FIG. 1A; FIG. 1B illustrates the prosthetic heart valve 30 in a compressed condition (e.g., when compressively retained within an outer catheter or sheath as described below). The prosthetic heart valve 30 includes a stent or stent frame 32 and a valve structure 34. The stent frame 32 can assume any of the forms mentioned above, and is generally constructed so as to be self-expandable from the compressed condition (FIG. 1B) to the normal, expanded condition (FIG. 1A). In other embodiments, the stent frame 32 can have a balloon-expandable configuration.

The valve structure 34 can assume a variety of forms, and can be formed, for example, from one or more biocompatible synthetic materials, synthetic polymers, autograft tissue, homograft tissue, xenograft tissue, or one or more other suitable materials. In some embodiments, the valve structure 34 can be formed, for example, from bovine, porcine, equine, ovine and/or other suitable animal tissues. In some embodiments, the valve structure 34 can be formed, for example, from heart valve tissue, pericardium, and/or other suitable tissue. In some embodiments, the valve structure 34 can include or form one or more leaflets 36. For example, the valve structure 34 can be in the form of a tri-leaflet bovine pericardium valve, a bi-leaflet valve, or another suitable valve. In some constructions, the valve structure 34 can comprise two or three leaflets that are fastened together at enlarged lateral end regions to form commissural joints, with the unattached edges forming coaptation edges of the valve structure 34. The leaflets 36 can be fastened to a skirt that in turn is attached to the frame 32. The upper ends of the commissure points can define an inflow portion 38 corresponding to a first or inflow end 40 of the prosthesis 30. The opposite end of the valve can define an outflow portion 42 corresponding to a second or outflow end 44 of the prosthesis 30. As shown, the stent frame 32 can have a lattice or cell-like structure, and optionally forms or provides crowns 46 and/or eyelets 48 (or other shapes) at the outflow and inflow ends 40, 44.

Figure 2:
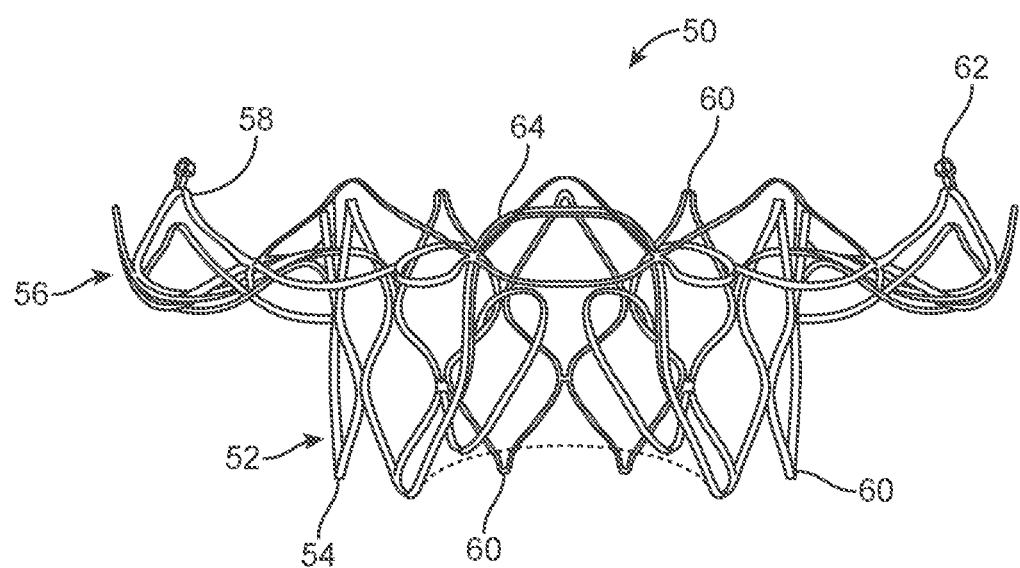
FIG. 2 is a side view of another exemplary heart valve stent useful with systems, devices and methods of the present disclosure and in a normal, expanded condition.

With the one exemplary construction of FIGS. 1A and 1B, the prosthetic heart valve 30 can be configured (e.g., sized and shaped) for replacing or repairing an aortic valve. Alternatively, other shapes are also envisioned, adapted to mimic the specific anatomy of the valve to be repaired (e.g., stented prosthetic heart valves useful with the present disclosure can alternatively be shaped and/or sized for replacing a native mitral, pulmonic or tricuspid valve). For example, FIG. 2 illustrates another non-limiting example of a stent frame 50 portion of another prosthetic heart valve with which the systems, devices and methods of the present disclosure are useful. In the normal or expanded condition of FIG. 2, the stent frame 50 can be sized and shaped for mitral valve implantation. Though not shown, the valve structure attached to the stent frame 50 defines an outflow portion 52 arranged at a first or outflow end 54, and an inflow portion 56 arranged at a second or inflow end 58. As compared to the stent frame 32 of FIG. 1A, the inflow portion 56 can exhibit a more pronounced change in shape relative to the corresponding outflow portion 52. Regardless, the stent frame 50 can be forced and constrained to a compressed condition (not shown, but akin to the shape of FIG. 1A) during delivery, and will self-expand to the natural condition of FIG. 2 upon removal of the constraining force(s). As reflected in FIG. 2, crowns 60 and/or eyelets 62 (or other shapes) optionally can be formed at one or both of the outflow and inflow ends 54, 58. Further, the stent frame 50 can optionally include or carry additional structural components, such as support arm(s) 64.

Figure 3A:
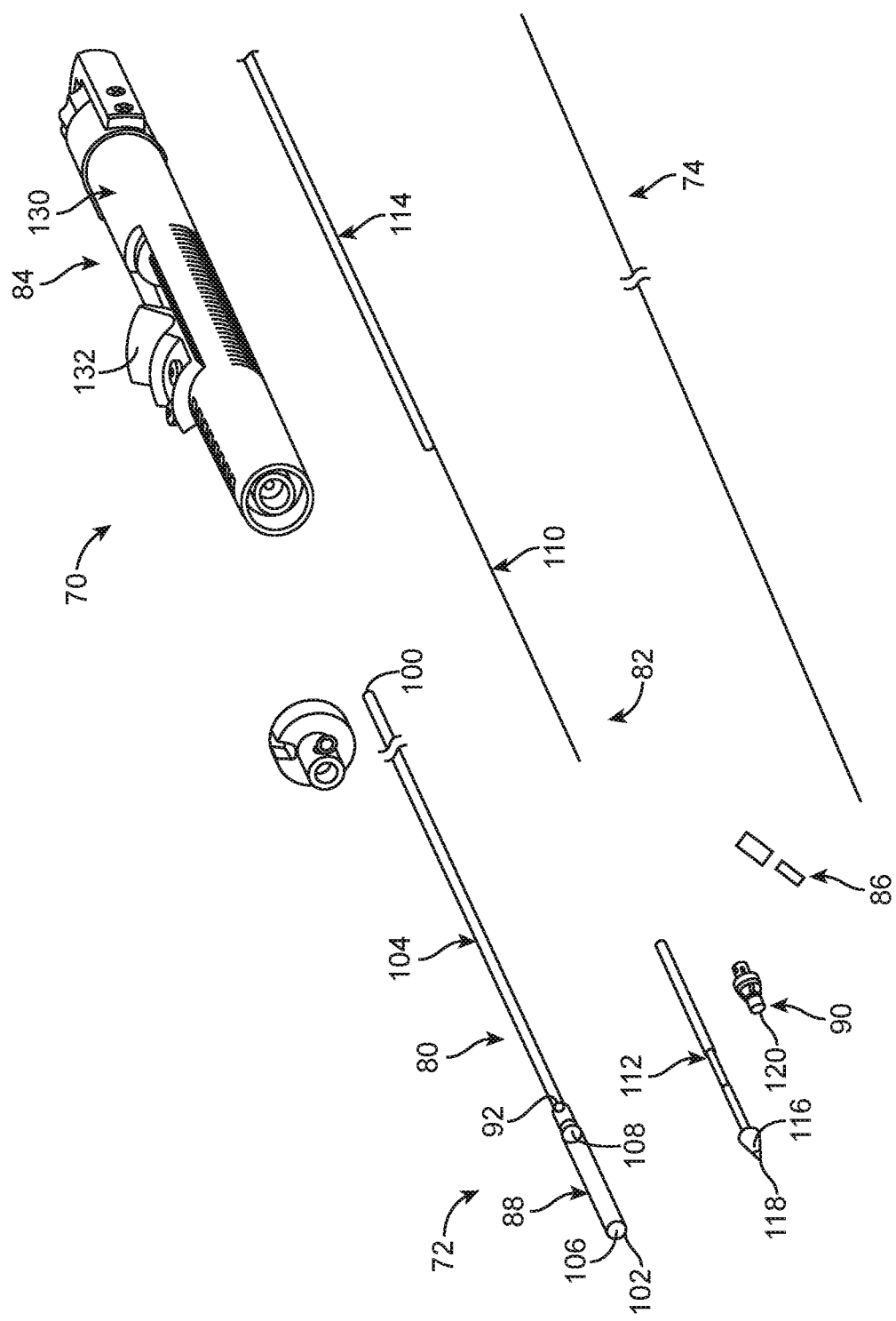
FIG. 3A is an exploded, perspective view of stented prosthetic heart valve delivery system in accordance with principles of the present disclosure.
Figure 3B:
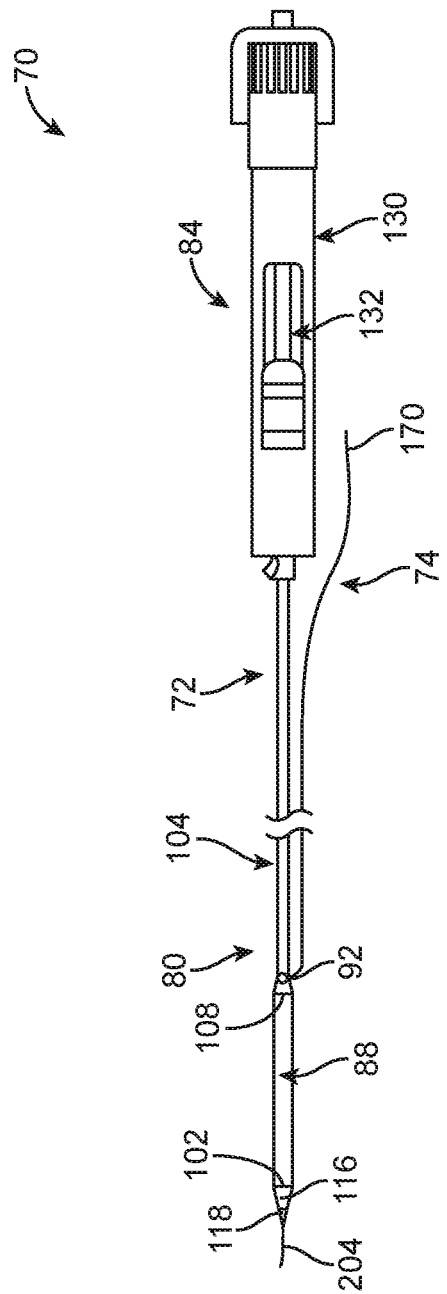
FIG. 3B is a side view of the delivery system of FIG. 3A.

With the above understanding of the stented prosthetic heart valves in mind, one embodiment of a delivery system 70 for percutaneously delivering the prosthesis is shown in simplified form in FIGS. 3A and 3B. The delivery system 70 includes a delivery device 72 and at least one guide wire 74. As described in greater detail below, the delivery device 72 is configured to slidably receive the guide wire 74 in a rapid exchange manner.

The delivery device 72 includes an outer sheath assembly 80, an inner shaft assembly 82, a handle assembly 84, and a connector assembly 86. Details on the various components are provided below. In general terms, however, the delivery device 72 provides a delivery condition in which a stented prosthetic heart valve (not shown) is loaded over the inner shaft assembly 82 and is compressively retained within a capsule 88 of the outer sheath assembly 80. For example, the inner shaft assembly 82 can include or provide a spindle or valve retainer 90 configured to selectively receive a corresponding feature (e.g., posts) provided with the prosthetic heart valve stent frame. The outer sheath assembly 80 can be manipulated to withdraw the capsule 88 proximally from over the prosthetic heart valve via operation of the handle assembly 84, permitting the prosthesis to self-expand and partially release from the inner shaft assembly 82. When the capsule 88 is retracted proximally beyond the valve retainer 90, the stented prosthetic heart valve can completely release or deploy from the delivery device 72. The delivery device 72 can optionally include other components that assist or facilitate or control complete deployment. Regardless, the connector assembly 86 facilitates loading of the guide wire 74 within a guide wire lumen (hidden) of the delivery device 72 (e.g., extending along the valve retainer 90) to a proximal guide wire exit port 92 in the outer sheath assembly 80. In the loaded arrangement of FIG. 3B, then, the guide wire 74 extends proximally from the proximal guide wire exit port 92 outside of the outer sheath assembly 80. Further, the connector assembly 86 (hidden in FIG. 3B) is configured to permit proximal movement of the outer sheath assembly 80 relative to the inner shaft assembly 82, such as when deploying the prosthetic heart valve.

Various features of the components 80-84 reflected in FIGS. 3A and 3B and as described below can be modified or replaced with differing structures and/or mechanisms. Thus, the present disclosure is in no way limited to the outer sheath assembly 80, the inner shaft assembly 82, or the handle assembly 84 as shown and described below. Any construction that generally facilitates compressed loading of a stented prosthetic heart valve over an inner shaft via a retractable outer sheath or capsule is acceptable. Further, the delivery device 72 can optionally include additional components or features, such as a flush port assembly, a recapture sheath (not shown), etc.

In some embodiments, the outer sheath assembly 80 defines proximal and distal ends 100, 102, and includes the capsule 88 and an outer shaft 104. The outer sheath assembly 80 can be akin to a catheter, defining a lumen 106 (referenced generally) that extends from the distal end 102, through the capsule 88 and at least a portion of the outer shaft 104. The lumen 106 can be open at the proximal end 100 (e.g., the outer shaft 104 can be a tube). The capsule 88 extends distally from the outer shaft 104, and in some embodiments has a more stiffened construction (as compared to a stiffness of the outer shaft 104) that exhibits sufficient radial or circumferential rigidity to overtly resist the expected expansive forces of the stented prosthetic heart valve (not shown) when compressed within the capsule 88. For example, the outer shaft 104 can be a polymer tube embedded with a metal braiding, whereas the capsule 88 includes a laser-cut metal tube that is optionally embedded within a polymer covering. Alternatively, the capsule 88 and the outer shaft 104 can have a more uniform or even homogenous construction (e.g., a continuous polymer tube). Regardless, the capsule 88 is constructed to compressively retain the stented prosthetic heart valve at a predetermined diameter when loaded within the capsule 88, and the outer shaft 104 serves to connect the capsule 88 with the handle assembly 84. The outer shaft 104 (as well as the capsule 88) is constructed to be sufficiently flexible for passage through a patient's vasculature, yet exhibits sufficient longitudinal rigidity to effectuate desired axial movement of the capsule 88. In other words, proximal retraction of the outer shaft 104 is directly transferred to the capsule 88 and causes a corresponding proximal retraction of the capsule 88. In other embodiments, the outer shaft 104 is further configured to transmit a rotational force or movement onto the capsule 88.

The guide wire exit port 92 is formed in the outer shaft 104 proximate the capsule 88. For example, the guide wire exit port 92 can be proximally spaced from a trailing end 108 of the capsule 88 by a distance on the order of 0.5-5.0 inches, although other locations are also acceptable. However, the guide wire exit port 92 is desirably distally spaced from the handle assembly 84 by a substantial distance sufficient to render the delivery device 70 to have rapid exchange attributes. The guide wire exit port 92 can assume a variety of shapes and sizes (e.g., circular, elongated slot, etc.) appropriate for slidably receiving the guide wire 74.

The inner shaft assembly 82 can have various constructions appropriate for supporting a stented prosthetic heart valve (not shown) relative to the outer sheath assembly 80, and includes the valve retainer 90, an intermediate shaft 110 and a distal shaft 112. The intermediate shaft 110 is sized to be slidably received within the outer sheath assembly 80 and serves as a transition to the valve retainer 90. The intermediate shaft 110 can be a solid or tubular structure, and in some embodiments has a rigid construction, such as a metal hypotube. Other, more flexible materials are also envisioned, such as flexible polymer tubing (e.g., PEEK). The intermediate shaft 110 can be configured for direct mounting to the handle assembly 84. In other embodiments, the inner shaft assembly 82 can further include a proximal shaft (e.g., tube) 114 interposed between the handle assembly 84 and the intermediate shaft 110. With these and related construction, the intermediate shaft 110 can have a more flexible construction as compared to the proximal shaft 114.

The distal shaft 112 is sized to be slidably received within the lumen 106 of the outer sheath assembly 80, and is configured for mounting to the valve retainer 90. The distal shaft 112 can be a flexible polymer tube embedded with a metal braid. Other constructions are also acceptable so long as the distal shaft 112 exhibits sufficient structural integrity to support a loaded, compressed stented prosthetic heart valve (not shown). A tip 116 is optionally formed by, or attached to, the distal shaft 112, and is akin to a nose cone having a distally tapering outer surface adapted to promote atraumatic contact with bodily tissue. The tip 116 can be fixed or slidable relative to the distal shaft 112. The distal shaft 112 forms a lumen (hidden) sized to slidably receive the guide wire 74 and that is open at a distal guide wire entry port 118.

The valve retainer 90 can assume various forms adapted to selectively receive a corresponding feature (e.g., posts) provided with the prosthetic heart valve stent frame and/or to directly support a portion of a length of the stent frame in the compressed condition. In some embodiments, the valve retainer 90 can have a spindle-like shape as shown and described, for example, in Dwork et al., U.S. Application Publication No. 2011/0098805 the entire teachings of which are incorporated by reference herein. The valve retainer 90 is configured for assembly to the intermediate shaft 110. The valve retainer 90 can be constructed for placement over the distal shaft 112, or alternatively for assembly between the distal shaft 112 and the intermediate shaft 110. Regardless, the valve retainer 90 forms a lumen (hidden) extending between a distal opening 120 and a proximal opening (hidden).

The handle assembly 84 generally includes a housing 130 and one or more actuator mechanisms 132 (referenced generally). The housing 130 maintains the actuator mechanism(s) 132, with the handle assembly 84 configured to facilitate sliding movement of the outer sheath assembly 80 relative to other components (e.g., the inner shaft assembly 82) by a user via, for example, manipulation of one or more of the actuator mechanisms 132. The housing 130 can have any shape or size appropriate for convenient handling by a user.

Figure 4:
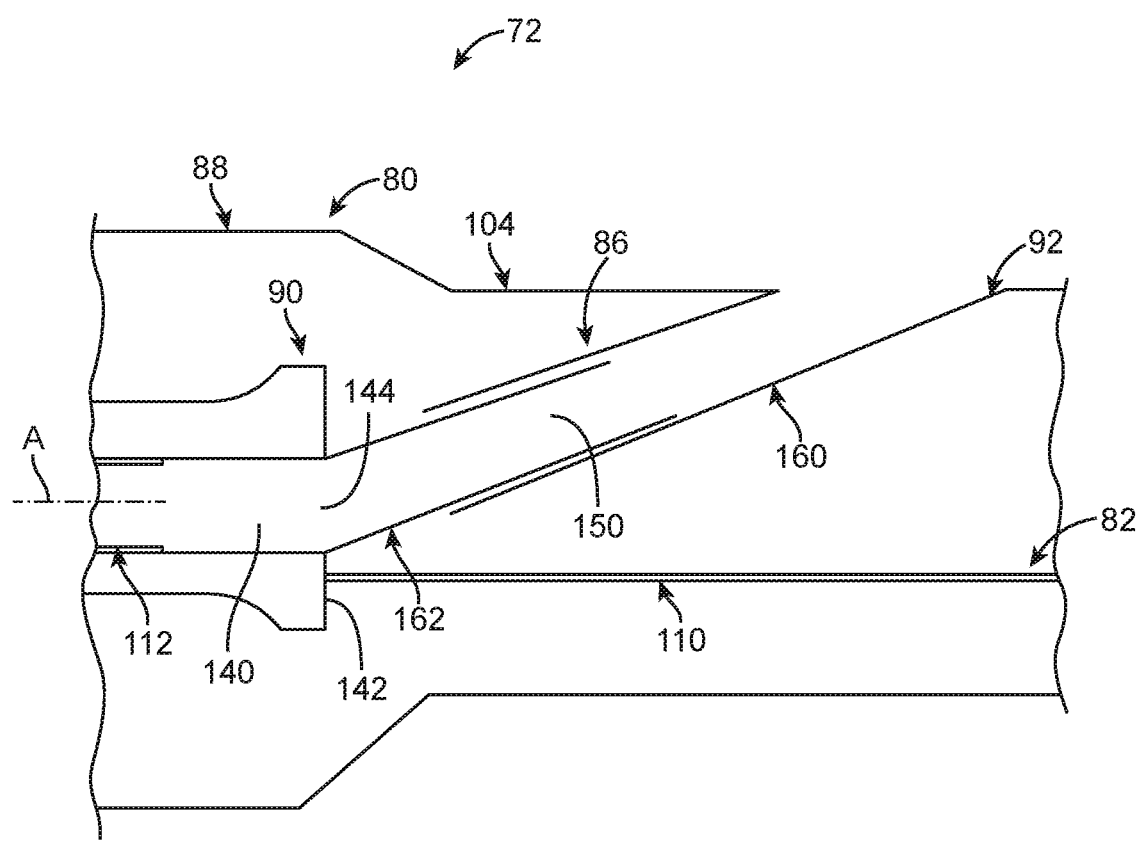
FIG. 4 is an enlarged, simplified cross-sectional view of a portion of the delivery system of FIG. 3A.

With the above general explanations of exemplary embodiments of the components 80-84 in mind, portions of one embodiment of the connector assembly 86 is shown in greater detail in FIG. 4. As a point of reference, FIG. 4 illustrates the delivery device 72 in the delivery condition, with the capsule 88 located over (and extending distally beyond) the valve retainer 90. A guide wire lumen 140 is also identified. The guide wire lumen 140 is open to the guide wire entry port 118 (FIG. 3A), and can be generated in various fashions as a function of the mounting arrangement between the valve retainer 90 and the distal shaft 112. The distal shaft 112 forms at least a portion of the guide wire lumen 140. With the exemplary embodiment of FIG. 4, the distal shaft 112 terminates within the valve retainer 90 such that the lumen of the valve retainer 90 is also "part" of the guide wire lumen 140. In other embodiments, the distal shaft 112 extends to a proximal face 142 of the valve retainer 90 such that the guide wire lumen 140 is entirely formed by the distal shaft 112. Regardless, the guide wire lumen 140 is open to a proximal opening 144, optionally formed in the proximal face 142 of valve retainer 90. Further, the intermediate shaft 110 is attached to the valve retainer 90, for example at the proximal face 142, at a location off-set from the proximal opening 144.

With the above conventions in mind, the connector assembly 86 establishes a guide wire passageway 150 between the proximal opening 144 (and thus the guide wire lumen 140) and the guide wire exit port 92. The guide wire passageway 150 is sized to slidably receive the guide wire 74 (FIG. 3A). The connector assembly 86 is configured to permit sliding movement of the outer sheath assembly 80 relative to the inner shaft assembly 82 (e.g., proximal retraction of the outer sheath assembly 80 from the delivery arrangement of FIG. 4), transitioning between a first state (FIG. 4) and a second state. In some embodiments, the connector assembly 86 has a telescope-like construction, and includes a first tube 160 and a second tube 162. The first and second tubes 160, 162 are slidably connected to one another and collectively define the guide wire passageway 150. The first tube 160 is attached to, or is formed by, the outer shaft 104, whereas the second tube 162 is attached to, or is formed by, the valve retainer 90. While FIG. 4 reflects that the first tube 160 has an inner diameter that is slightly greater than an outer diameter of the second tube 162 (such that the second tube 162 is slidably received within the first tube 160), an opposite construction is equally acceptable.

The first and second tubes 160, 162 can be formed of the same or similar material, and in some embodiments are each a thin wall plastic extruded part. Other materials, such as metals, are also envisioned. The first tube 160 can be mounted to the outer shaft 104 at the guide wire exit port 92 in various fashions as a function of the selected materials. For example, the first tube 160 can be adhered, welded, etc., to the outer shaft 104. In other embodiments, the first tube 160 is manufactured as part of the outer shaft 104. Regardless, the first tube 160 optionally incorporates a thin wall construction, at least at the point of intersection with the outer shaft 104, so as to readily permit slight pivoting movement of the first tube 160 relative to the outer shaft 104.

Similarly, the second tube 162 can be mounted to the valve retainer 90 at the proximal opening 144 in various fashions as a function of the selected materials. For example, the second tube 162 can be adhered, welded, etc., to the valve retainer 90 (e.g., at the proximal face 142). The second tube 162 optionally incorporates a thin wall construction, at least at the point of intersection with the valve retainer 90, so as to readily permit slight pivoting movement of the second tube 162 relative to the valve retainer 90.

In some embodiments, the guide wire lumen 140 extends along a longitudinal axis A of the valve retainer 90, such that the proximal opening 144 is centrally located along the proximal face 142. With this construction, the second tube 162 also extends from a central location of the proximal face 142, and the intermediate shaft 110 is radially off-set from the longitudinal axis A at the point of attachment to the valve retainer 90. Stated otherwise, with some constructions of the present disclosure, the intermediate shaft 110 and the valve retainer 90 are not longitudinally aligned. Other configurations are also envisioned. For example, the guide wire lumen 140 can deviate from the longitudinal axis A, non-centrally locating the proximal opening 144, and thus the second tube 162, along the proximal face 142. Alternatively, the proximal opening 144 can be formed in a side of the valve retainer 90. With either construction, the intermediate shaft 110 can then be aligned with the longitudinal axis A if desired. Notably, while the intermediate shaft 110 optionally is a metal hypotube, in other embodiments, the intermediate shaft 110 can be a solid body that does not otherwise form an internal lumen. Because the guide wire 74 (FIG. 3A) does not extend through the intermediate shaft 110, the intermediate shaft 110 of the present disclosure can have a smaller diameter as compared to inner shafts typically employed with stented prosthetic heart valve delivery devices.

In yet other embodiments, at least a portion of the intermediate shaft 110 is tubular and is connected to the valve retainer 90 at the proximal opening 144. The second tube 162, in turn, is connected to the intermediate shaft 110 proximal to the valve retainer 90 with the lumen of the second tube 162 being open to the lumen of the intermediate shaft 110. With this alternative construction, then, the intermediate shaft 110 can be connected to the valve retainer 90 along the longitudinal axis A, with the guide wire lumen 140 effectively continuing from the valve retainer 90 through a portion of the intermediate shaft 110 and open to the second tube 162.

Figure 5A:
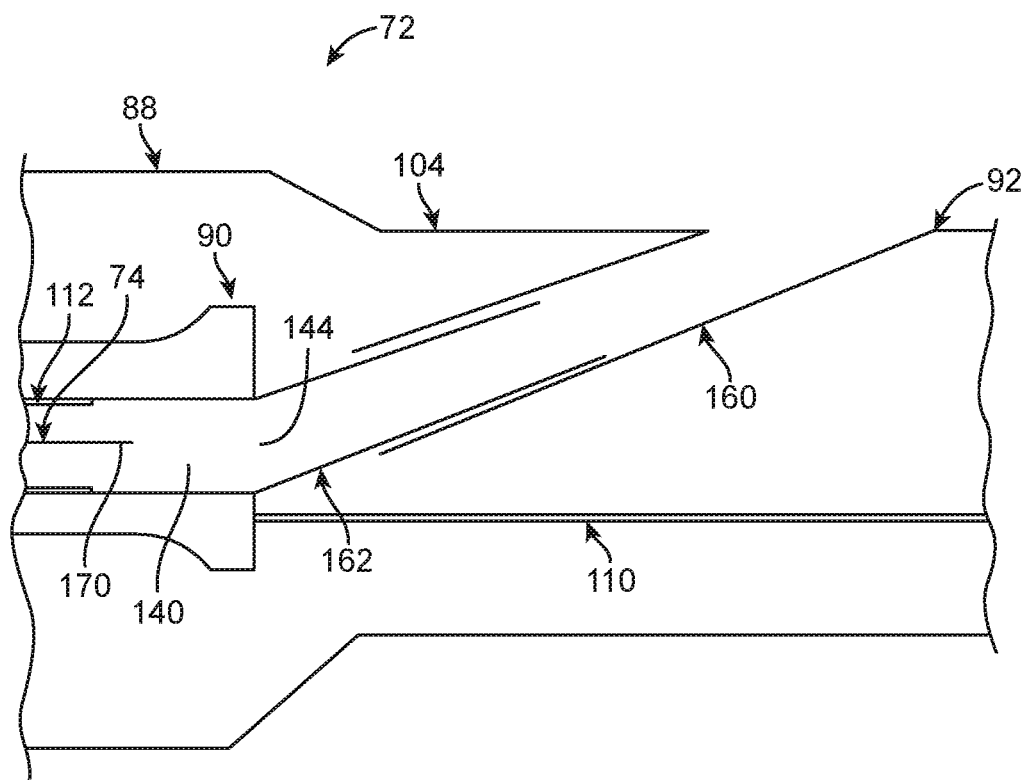
FIGS. 5A-5C illustrate assembly of the system of FIG. 3A, including loading of a delivery device over a guide wire.

FIG. 5A illustrates an initial stage of loading the delivery device 72 on to the guide wire 74, with the delivery device 72 in the delivery condition (and the connector assembly 86 in the first state). As a point of reference, the delivery device 72 will typically be loaded with a stented prosthetic heart valve prior to loading on to the guide wire 74; for ease of illustration, the stented prosthetic heart valve is omitted from the views of FIGS. 5A-5C, but can assume any of the forms described above. With additional reference to FIG. 3A, a proximal end 170 of the guide wire 74 is first inserted into the distal guide wire entry port 118, and then guided through the guide wire lumen 140 along the distal shaft 112. In the arrangement of FIG. 5A, the proximal end 170 has subsequently progressed (via distal advancement of the delivery device 72 over the guide wire 74 and/or proximal insertion of the guide wire 74 into the delivery device 72) to location within the valve retainer 90.

As the guide wire 74 is further progressed relative to the delivery device 72 from the arrangement of FIG. 5A, the proximal end 170 passes through the proximal opening 144 and enters the second tube 162. With further advancement, the guide wire passageway 150 directs the proximal end 170 to the guide wire exit port 92. In the loaded condition of FIG. 5B, then, the guide wire 74 is slidably disposed within the guide wire lumen 140 and the guide wire passageway 150, and extends proximally from the guide wire exit port 92 along an exterior of the outer shaft 104, for example to a region of (but not within) the handle assembly 84 (FIG. 3B).

Figure 5B:
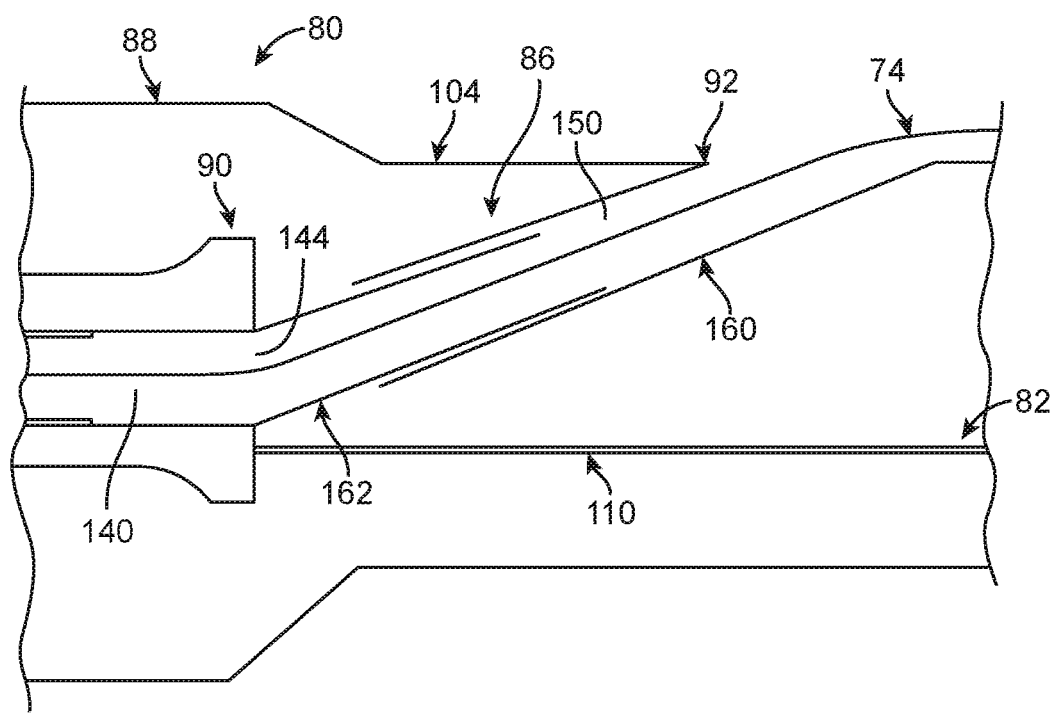
Figure 5C:
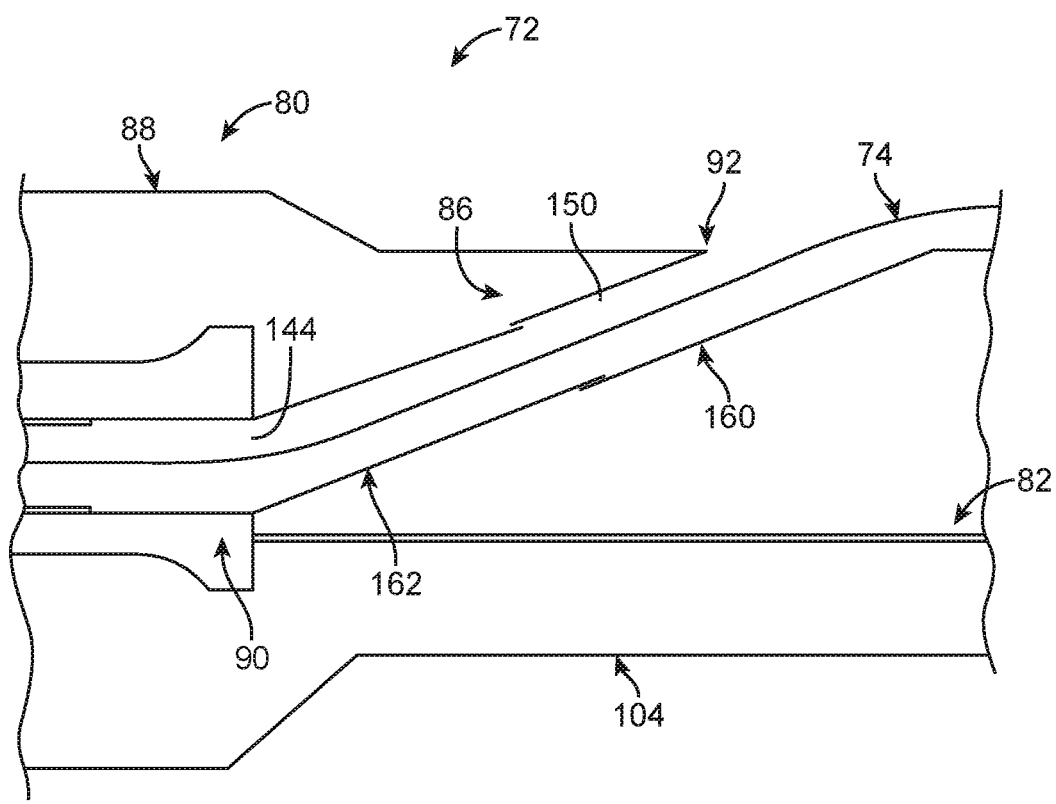

While loaded over the guide wire 74, the delivery device 72 can be transitioned from the delivery condition of FIGS. 5A and 5B to the deployment condition of FIG. 5C by proximally retracting the outer sheath assembly 80 relative to the inner shaft assembly 82 (and/or vice-versa). With this movement, the connector assembly 86 transitions from the first state of FIGS. 5A and 5B to the second state of FIG. 5C. More particularly, as the outer sheath and inner shaft assemblies 80, 82 are moved relative to one another, the first tube 160 slides along the second tube 162 and/or vice-versa, accommodating the increasing longitudinal distance between the guide wire exit port 92 and the proximal opening 144. In some embodiments, the first and second tubes 160, 162 are dimensioned so as to remain in contact with one another in the delivery condition such that the guide wire passageway 150 is complete in the second state. In other configurations, a distance of travel of the outer sheath and inner shaft assemblies 80, 82 relative to one another in achieving the deployment condition is greater than the length of interface between the first and second tubes 160, 162 in the first state (FIG. 5B), such that the first tube 160 alternatively disconnects from the second tube 162 in the second state. Regardless, the guide wire 74 freely slides within the guide wire passageway 150 as the first and second tubes 160, 162 are transitioned to the second state (e.g., the guide wire 74 can remain spatially stationary as the outer sheath assembly 80 is proximally retracted), with the first tube 160 slightly deflecting relative to the outer shaft 104 and the second tube 162 slightly deflecting relative to the valve retainer 90 in accordance with the changing geometries.

The connector assemblies of the present disclosure are configured to accommodate relative movements of the outer sheath assembly 80 relative to the inner shaft assembly 82 for a plethora of different delivery device designs. As a point of reference, the distance of travel of the outer sheath assembly 80 relative to the inner shaft assembly 82 in deploying the stented prosthetic heart valve (not shown) can be on the order of 50-100 mm, for example about 70 mm.

Figure 6A:
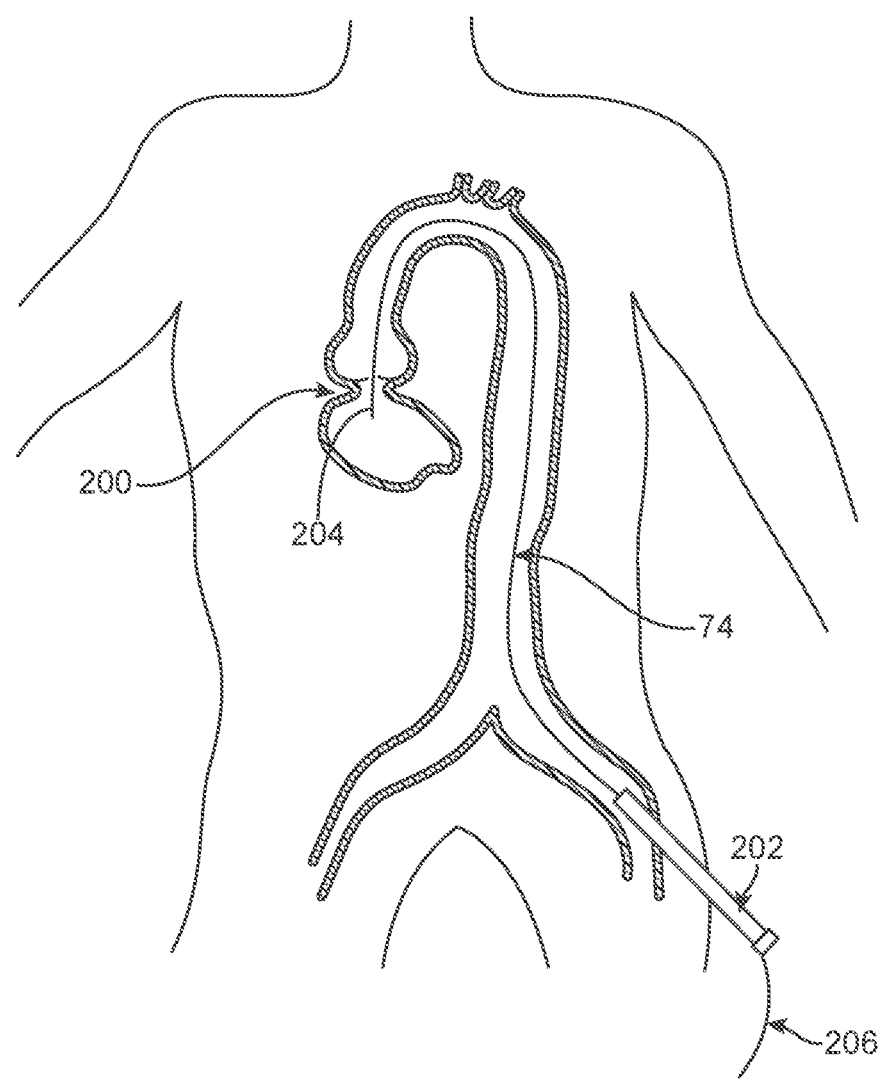
FIGS. 6A-6C illustrate portions of a method of implanting a stented prosthetic heart valve with the system of FIG. 3A and in accordance with the principles of the present disclosure.

The delivery system 70 can be used in performing a therapeutic procedure on a defective heart valve of a patient. For example, FIG. 6A illustrates an aortic valve 200 target site. An introducer 202 can be used to initially place the guide wire 74 into the patient, with a distal end 204 of the guide wire 74 being advanced in a retrograde manner through a cut-down to the femoral artery, into the patient's descending aorta, over the aortic arch, through the ascending aorta, and across the defective aortic valve 200. A relatively short length 206 of the guide wire 74 remains outside of the introducer 202, and is less than a length of the delivery device 72 (FIG. 3B).

Figure 6B:
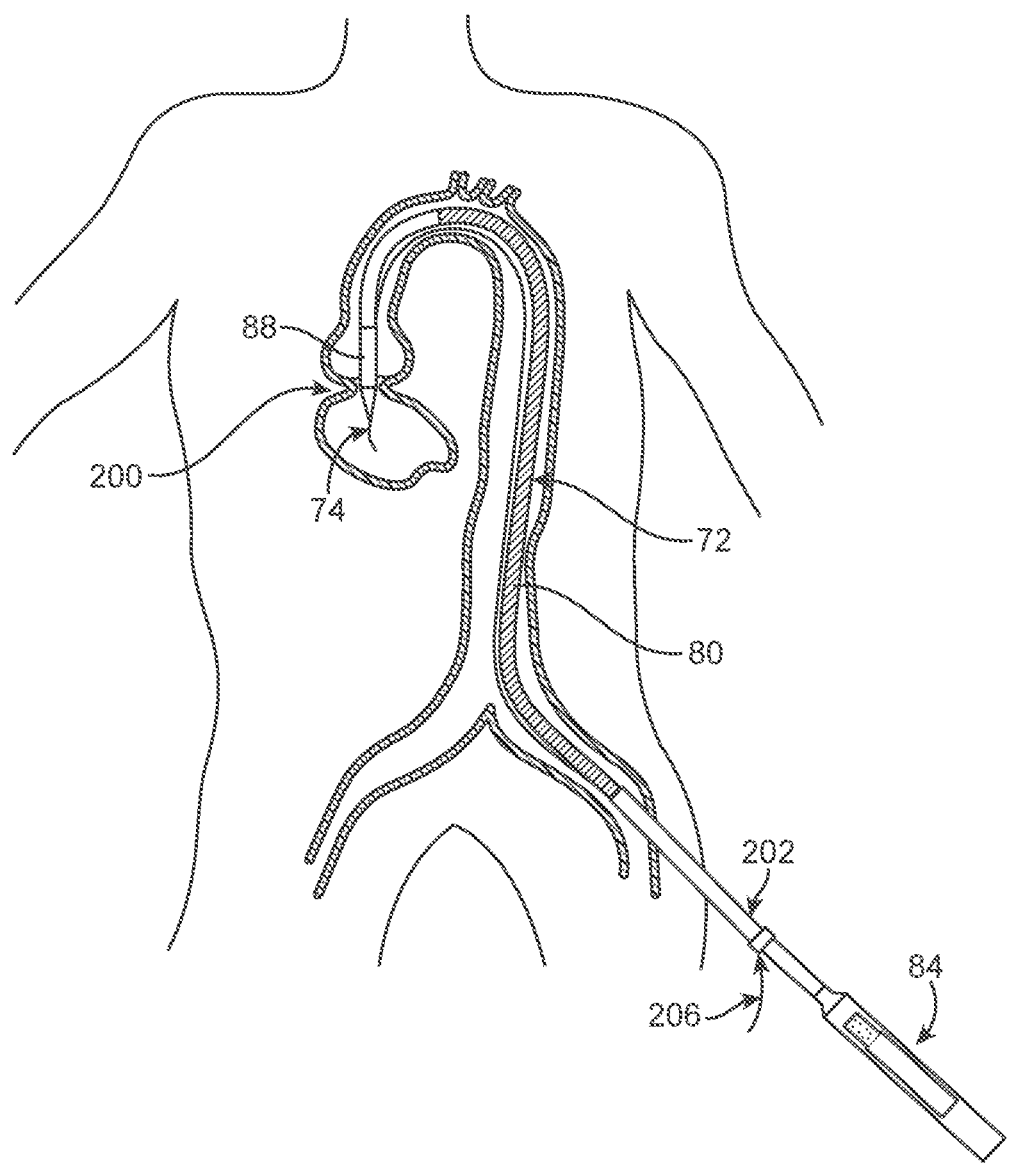
Figure 6C:
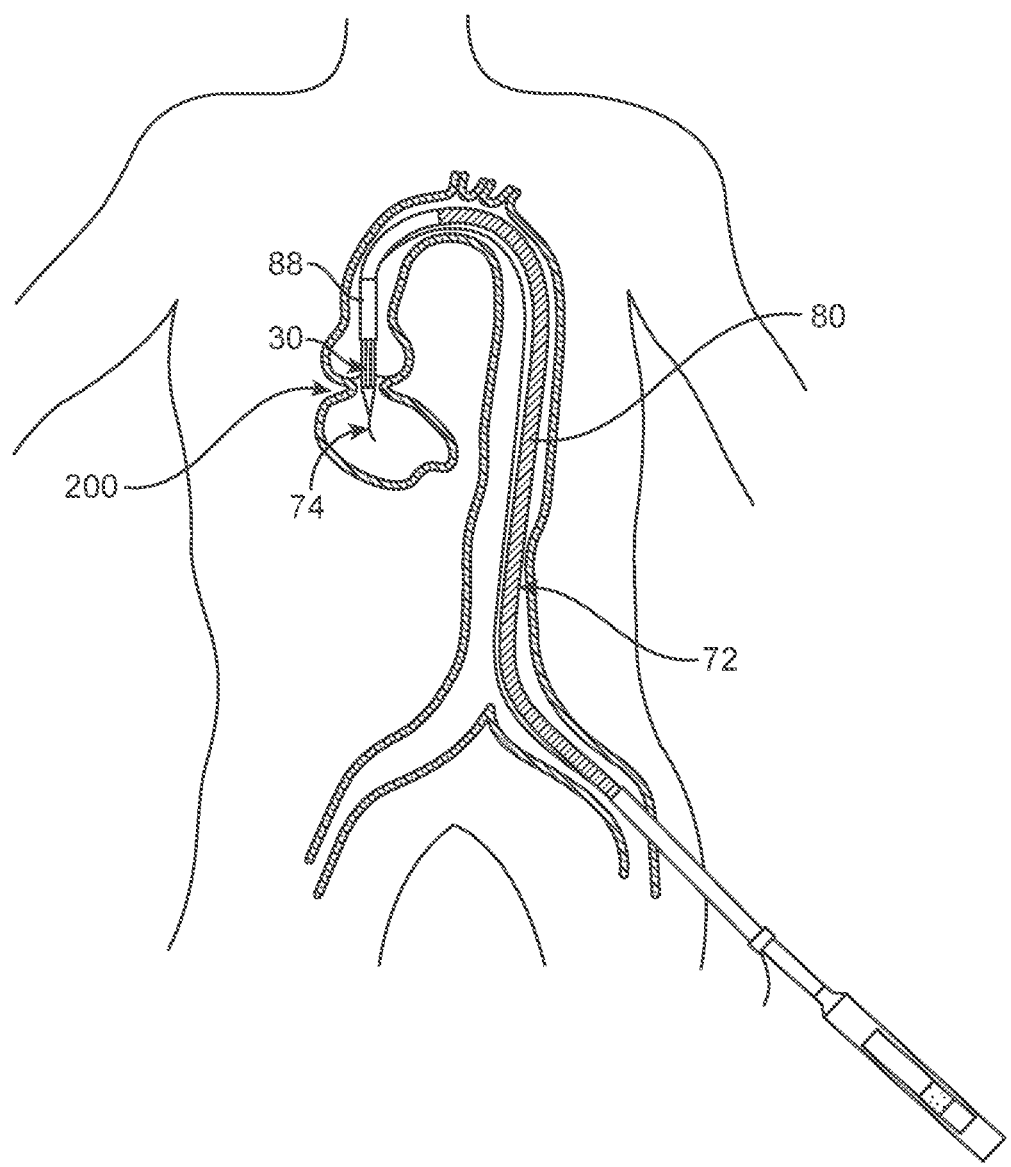

The delivery device 72 (in the delivery condition with a stented prosthetic heart valve (hidden)) is then loaded on to the available length 206 of the guide wire 74 as described above and as generally reflected by FIG. 6B. The delivery device 72 is advanced over the guide wire 74, bringing the capsule 88 to a desired location relative to the native aortic valve 200 (e.g., slightly proximal the native valve 200). The handle assembly 84 is then operated to retract the outer sheath assembly 80 relative to the inner shaft assembly 82 (referenced generally) to effectuate deployment of the prosthetic heart valve 30 as in FIG. 6C. With this movement, the outer sheath assembly 80 slides over or relative to the guide wire 74 such that the guide wire 74 remains spatially stationary. In some instances, prior to full deployment of the stented prosthetic heart valve 30, an optional partial deployment and evaluation procedure can be performed in which the prosthetic heart valve 30 is partially deployed from the delivery device 72 and a position of the so-deployed region relative to the implant site is evaluated. If desired, the delivery device 72 can optionally be configured to effectuate recapture of the partially deployed prosthesis, for example by distally advancing the capsule 88 relative to the inner shaft assembly 82 and back over the prosthetic heart valve 30. Under these circumstances, the connector assembly 86 (FIG. 4) can be configured to permit this relative movement.

Figure 7:
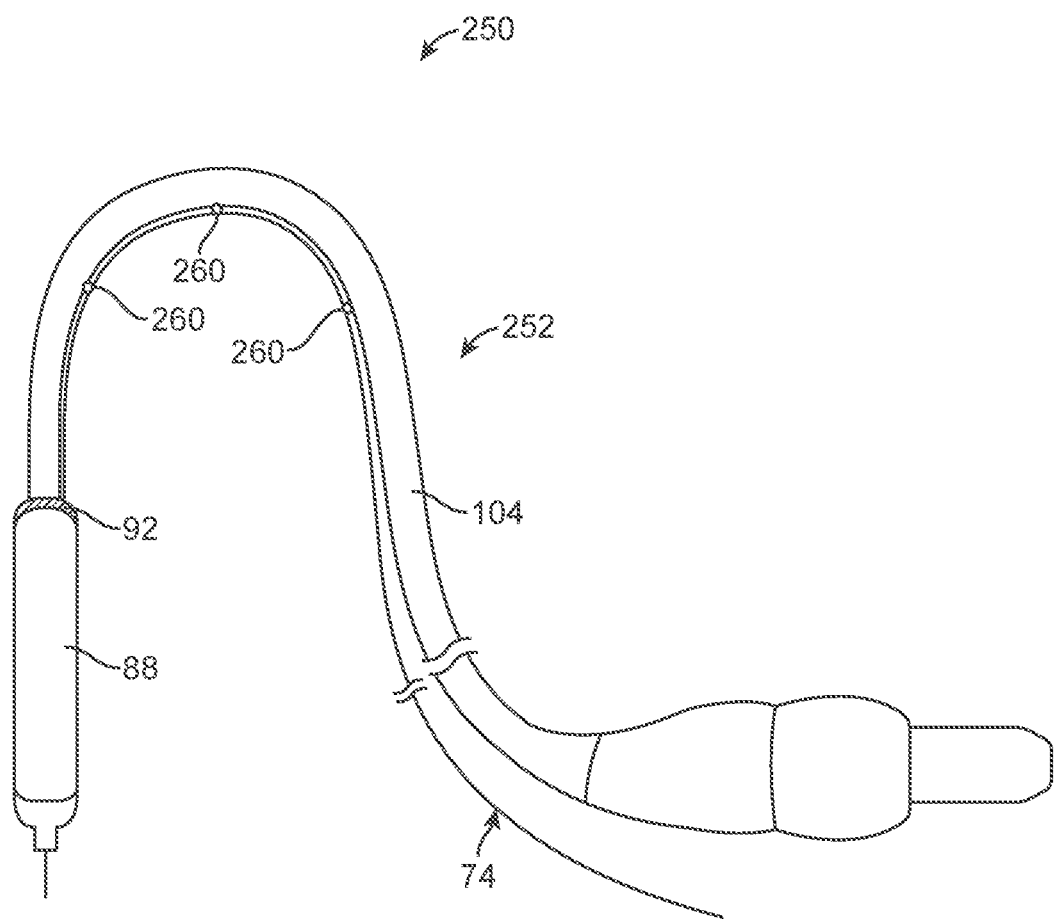
FIG. 7 is a simplified side view of another stented prosthetic heart valve delivery system in accordance with principles of the present disclosure.

The devices, systems, and methods of the present disclosure can be useful in performing a therapeutic procedure on any defective valve of the patient's heart (i.e., aortic, mitral, pulmonic or tricuspid), and can also be utilized to deploy a replacement valve into a previously implanted prosthetic heart valve. With the aortic valve repair procedures of FIGS. 6A-6C, and with other procedures, the anatomical pathway may subject the delivery system 70 to significant turns or bends (e.g., as the delivery device system traverses the aortic arch). To better ensure that the guide wire 74 generally follows a curved shape of the delivery device 72 along the anatomical bend but does not slide with the delivery sheath assembly 80 due to a frictional interface along the bend (thus avoiding "cheese-wiring" of the anatomical tissue), the delivery devices of the present disclosure can optionally include one or more support bodies along an exterior of the outer sheath assembly 80. For example, FIG. 7 illustrates another delivery system 250 in accordance with principles of the present disclosure in simplified form, and includes a delivery device 252 and the guide wire 74. The delivery device 252 can be highly akin to the delivery device 72 (FIGS. 3A and 3B) described above, and can include any or all of the features previously described. In addition, the delivery device 252 includes one or more support bodies 260 along an exterior of the outer shaft 104 proximal the guide wire exit port 92. The support bodies 260 are generally configured to slidably receive the guide wire 74, and generally retain the guide wire 74 in close but spaced proximity to the outer shaft 104. The support bodies 260 can assume a variety of forms, and in some embodiments are akin to an eyelet. The number and location of the support bodies 260 relative to the capsule 88 corresponds with the expected, small radius bend (due to the anatomical pathway) in the delivery device 252 upon achieving the final delivery position. The support bodies 260 ensure that the guide wire 74 remains connected to, but slightly spaced from, the delivery device 252 along the tight bend or turn, and thus minimizes surface contacts between the guide wire 74 and the delivery device 252 and subsequently frictional forces between the guide wire 74 and the delivery device 252.

Figure 8A:
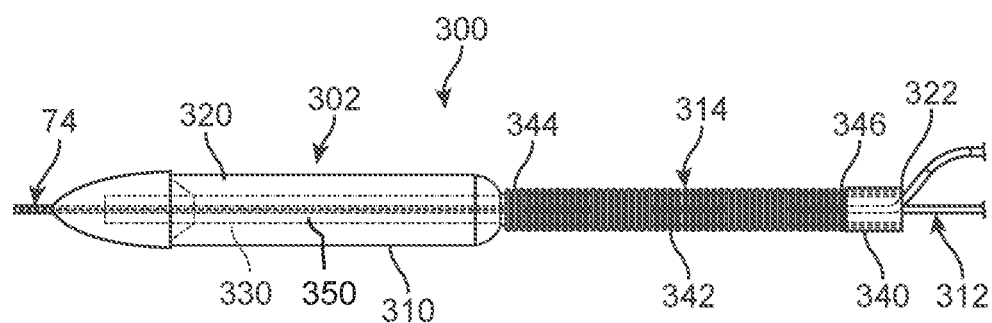
FIGS. 8A and 8B are simplified, cross-sectional views of portions of another stented prosthetic heart valve delivery system in accordance with principles of the present disclosure.
Figure 8B:
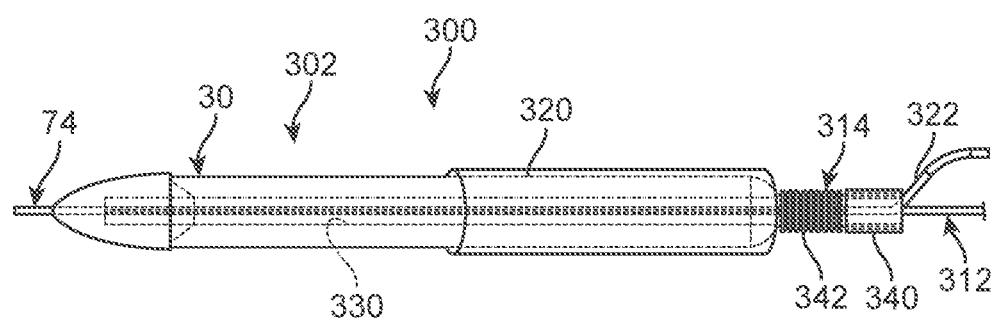

Portions of another delivery system 300 in accordance with principles of the present disclosure are shown in FIGS. 8A and 8B. The delivery system 300 includes a delivery device 302 and the guide wire 74. The delivery device 302 can assume a wide variety of forms, and generally includes an outer sheath assembly 310, an inner shaft assembly 312, and a relief assembly 314. The outer sheath assembly 310 can assume any of the configurations described above, and in general includes or defines a capsule 320 and a guide wire exit port 322 (referenced generally). The inner shaft assembly 312 can also assume any of the forms described above, and defines a guide wire lumen 330. The relief assembly 314 includes a base 340 and a coil spring 342. The base 340 is attached to the inner shaft assembly 312. The coil spring 342 is co-axially received over the inner shaft assembly 312, located between the capsule 320 and the base 340. More particularly, a distal end 344 of the coil spring 342 is located proximate the capsule 320, and a proximal end 346 of the coil spring 342 is located proximate the base 340.

In the delivery condition of FIG. 8A, the guide wire 74 is slidably received within the guide wire lumen 330. The guide wire 74 exits the guide wire lumen 330 proximate the distal end 344 of the coil spring 342, and extends along a spacing between the coil spring 342 and the inner shaft assembly 312. The guide wire 74 is further slidably received within the base 340, and extends proximally from the guide wire exit port 322. The prosthetic valve 30 (FIG. 8B) is compressed over a support segment 350 (referenced generally) of the inner shaft assembly 312 and is retained within the capsule 320. Upon transitioning of the delivery device 302 to the deployment condition of FIG. 8B, the movement of the capsule 320 in proximally retracting from the support segment 350 (FIG. 8A) causes the coil spring 342 to compress in a direction of the base 340. The guide wire 74 freely resides in the spacing between the coil spring 342 and the inner shaft assembly 312 such that the guide wire 74 experiences minimal, if any, friction-type forces as the prosthetic valve 30 (schematically illustrated) is deployed.

Portions of another delivery system 400 in accordance with principles of the present disclosure are shown in FIG. 9. The delivery system 400 includes a delivery device 402 and the guide wire 74. The delivery device 402 can assume a wide variety of forms as described above, and generally includes an outer sheath assembly 410, an inner shaft assembly 412 (referenced generally), and a relief assembly 414. The outer sheath assembly 410 can have any of the forms described above, and forms a capsule 420 and an outer shaft 422 defining a guide wire exit port 424. The inner shaft assembly 412 can also have any of the forms described above, and defines a guide wire lumen 430. The relief assembly 414 can be formed in tandem with the inner shaft assembly 412, and includes a plurality of clips 440. The clips 440 can have a C-shape construction, configured to facilitate captured passage of the guide wire 74.

More particularly, one of the clips 440 is shown in greater detail in FIG. 10A. The clip 440 can be a C-clip, defined by overlapping, first and second ends 442, 444. As reflected by FIGS. 10B and 10C, the clip ends 442, 444 can be deflected away from one another to permit insertion of the guide wire 74 into an interior space of the clip 440. Once the guide wire 74 is inserted, the clip 440 self-reverts back to the natural state of FIG. 10C, thereby capturing the guide wire 74.

Returning to FIG. 9, the relief assembly 414 facilitates loading of the guide wire 74 into the guide wire lumen 430, and directs the guide wire 74 from the guide wire lumen 430 to the guide wire exit port 424. The guide wire 74 is thus slidably received by the delivery device 402, with a location of the guide wire exit port 424 being akin to a rapid exchange design.

Although the present disclosure has been described with reference to preferred embodiments, workers skilled in the art will recognize that changes can be made in form and detail without departing from the spirit and scope of the present disclosure.

What is claimed is:

1. A delivery device for implanting a stented prosthetic heart valve, the device comprising:
   a handle;
   an inner shaft assembly extending from the handle and including a shaft and a valve retainer, the inner shaft assembly defining a guide wire lumen;
   a capsule slidably received over the inner shaft assembly, wherein the capsule is configured to compressibly retain a stented prosthetic heart valve;
   a guide wire exit port proximal of the capsule and distal of the handle;
   a relief assembly proximal the capsule, distal the guide wire exit port, and co-axially received over the inner shaft assembly, wherein:
      a distal end of the relief assembly is proximate a proximal end of the capsule,
      a proximal end of the relief assembly is distal the guide wire exit port,
      a guide wire receiving spacing is defined between the relief assembly and the inner shaft assembly for passage of a guide wire from the guide wire lumen to the guide wire exit port, the guide wire receiving spacing being external the inner shaft assembly,
      the relief assembly includes a component selected from the group consisting of a coil spring and a plurality of clips.

2. The delivery device of claim 1, wherein the delivery device is configured to provide a delivery condition in which a stented prosthetic heart valve is compressed over a support segment of the inner shaft assembly and retained within the capsule.

3. The delivery device of claim 2, wherein the delivery device is further configured to provide a deployment condition in which the capsule is proximally retracted from the support segment.

4. The delivery device of claim 1, wherein the relief assembly comprises a coil spring and a base, a distal end of the coil spring being proximate the proximal end of the capsule and a proximal end of the coil spring is spatially anchored relative to the capsule by the base such that movement of the capsule in a proximal direction compresses the coil spring.

5. The system of claim 1, wherein the relief assembly comprises a plurality of clips.

6. The system of claim 5, wherein the plurality of clips includes a C-clip.

7. A delivery system for implanting a stented prosthetic heart valve, the system comprising:
   a delivery device comprising:
      a handle,
      an inner shaft assembly extending from the handle and including a shaft and a valve retainer, the inner shaft assembly defining a guide wire lumen,
      a capsule slidably received over the inner shaft assembly, wherein the capsule is configured to compressibly retain a stented prosthetic heart valve,
      a guide wire exit port proximal of the capsule and distal of the handle, and
      a relief assembly proximal the capsule, distal the guide wire exit port, and co-axially received over the inner shaft assembly, wherein:
         a distal end of the relief assembly is proximate a proximal end of the capsule,
         a proximal end of the relief assembly is distal the guide wire exit port,
         a guide wire receiving spacing is defined between the relief assembly and the inner shaft assembly, the guide wire receiving spacing being external the inner shaft assembly,
         the relief assembly includes a component selected from the group consisting of a coil spring and a plurality of clips; and
   a guide wire;
   wherein the system is configured to provide a delivery state in which:
      the guide wire is slidably disposed within the guide wire lumen and the guide wire receiving spacing,
      the guide wire exits the delivery device at the guide wire exit port and is free of the delivery device proximal the guide wire exit port.

8. The system of claim 7, wherein the delivery device is transitionable from a delivery condition to a deployment condition with the system in the delivery state, the transition including proximal retraction of the capsule, and further wherein the guide wire freely resides in the guide wire receiving spacing during transition of the delivery device from the delivery condition to the deployment condition.

9. The system of claim 7, wherein the delivery device is configured to provide a delivery condition in which a stented prosthetic heart valve is compressed over a support segment of the inner shaft assembly and retained within the capsule.

10. The system of claim 9, wherein the delivery device is further configured to provide a deployment condition in which the capsule is proximally retracted from the support segment.

11. The system of claim 7, wherein the relief assembly comprises a coil spring and a base, a distal end of the coil spring being proximate the proximal end of the capsule and a proximal end of the coil spring is spatially anchored relative to the capsule by the base such that movement of the capsule in a proximal direction compresses the coil spring.

12. The system of claim 7, wherein the relief assembly comprises a plurality of clips.

13. The system of claim 12, wherein the plurality of clips includes a C-clip.

* * * * *